United States Patent [19]

Hallenbach et al.

[11] Patent Number: 4,740,520
[45] Date of Patent: Apr. 26, 1988

[54] USE OF THIENYLUREA DERIVATIVES AS SELECTIVE FUNGICIDES

[75] Inventors: Werner Hallenbach, Langenfeld; Hans Lindel, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 931,293

[22] Filed: Nov. 14, 1986

[30] Foreign Application Priority Data

Nov. 26, 1985 [DE] Fed. Rep. of Germany ....... 3541631

[51] Int. Cl.$^4$ ............................................. A01N 43/06
[52] U.S. Cl. ................................................ 514/447
[58] Field of Search ........................................ 514/447

[56] References Cited

U.S. PATENT DOCUMENTS 3,823,161 7/1974 Lesser ................................. 549/69
4,472,425 9/1984 Sandmeier et al. ................ 514/447

OTHER PUBLICATIONS

Arch. Pharm. (Weinheim), 312, pp. 726–733 (1979).
Devani et al, "Synthesis of 3-Substituted Thieno...", J. of Pharmaceutical Sciences, vol. 65, No. 5 (May 1976), pp. 660–664.
92:76205r, Visnu Ji Ram, "Tiphenes, Pyrazolothiaophenes...", Chem. Abstr., v. 92, No. 9 (Mar. 1980), p. 650.
J. R. Coley-Smith, "The Biology of Botrytis", Article, Academic Press (1980), pp. vii–ix and 15–16, R. B. Maude, "Disease Control", pp. 275–292.
Fröhlich et al, "Pests and Diseases of Tropical Crops and their Control", Pergamon Press (1970), pp. 39, 97, 125, 131, 187, 268 and 292.
"Index of Plant Diseases in the United States", U.S. Dept. of Agric., Handbook No. 165 (Aug. 1960), vol. 51, No. 3, pp. 235 and 237.

Primary Examiner—Allen J. Robinson
Attorney, Agent, or Firm—Sprung Horn Kramer & Woods

[57] ABSTRACT

A method of combating fungi which comprises applying to such fungi or to a fungus habitat a fungicidally effective amount of a thienylurea derivative of the formula

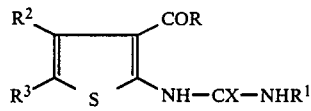

in which
X is oxygen or sulphur,
R is $C_1$–$C_4$-alkoxy,
$R^1$ is $C_3$–$C_4$-alkyl, and
$R^2$ and $R^3$ each independently is $C_1$–$C_4$-alkyl and one of them may also be hydrogen.

13 Claims, No Drawings

USE OF THIENYLUREA DERIVATIVES AS SELECTIVE FUNGICIDES

The present invention relates to the use of thienylurea derivatives as a selective fungicide against Botrytis fungi.

It has already been disclosed that certain thienylureas, such as, for example, 1-(4,5-dimethyl-3-ethoxycarbonyl-2-thienyl)-3-methylurea, have good fungicidal activity (see, for example, U.S. Pat. No. 3,823,161). However, nothing is known about the activity against Botrytis fungi, which is of great interest from the economic point of view.

It has been found that, because of their particularly good selective fungicidal activity against Botrytis fungi, in particular the compounds of the formula (I)

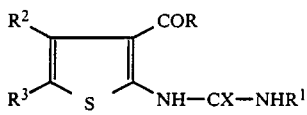

in which

X represents oxygen or sulphur,

R represents $C_1$–$C_4$-alkoxy, $R^1$ represents $C_3$–$C_4$-alkyl, and $R^2$ and $R^3$ each independently represents $C_1$–$C_4$-alkyl and one of them may also represent hydrogen.

can be used for combating these fungi.

Surprisingly, the thienylurea derivatives of the formula (I) have a substantially greater selective fungicidal action against Botrytis fungi than the compound 1-(4,5-dimethyl-3-ethoxycarbonyl-2-thienyl)-3-methylurea, which is known from the prior art (see, for example, U.S. Pat. No. 3,823,161).

The $C_3$–$C_4$-alkyl radical $R^1$ denotes straight-chain or branched alkyl having 3 or 4 carbon atoms. n-Propyl, i-propyl, n-butyl, i-butyl, sec.-butyl and tert.-butyl may be mentioned as examples.

The $C_1$–$C_4$-alkoxy radical R denotes straight-chain or branched alkoxy having 1 to 4 carbon atoms. Methoxy, ethoxy, n-propoxy, i-propoxy, n-butoxy, i-butoxy, sec.-butoxy and tert.-butoxy may be mentioned as examples.

The $C_1$–$C_4$-alkyl radicals $R^2$ and $R^3$ denote straight-chain or branched alkyl having 1 to 4 carbon atoms. Methyl, ethyl, n-propyl, i-propyl, n-butyl, i-butyl, sec.-butyl or tert.-butyl may be mentioned as examples.

X preferably represents oxygen.

Formula (I) gives a general definition of the thienylurea derivatives to be used according to the invention. In this formula, X preferably represents oxygen, R preferably represents methoxy, ethoxy, n-propoxy, i-propoxy, n-butoxy, i-butoxy, sec.-butoxy and tert.-butoxy, $R^1$ preferably represents n-propyl, i-propyl, n-butyl, i-butyl, sec.-butyl and tert.-butyl, $R^2$ preferably represents hydrogen, methyl, ethyl, n-propyl, i-propyl, n-butyl, i-butyl, sec.-butyl and tert.-butyl and $R^3$ preferably represents methyl, ethyl, n-propyl, i-propyl, n-butyl, i-butyl, sec.-butyl and tert.-butyl, or X, R and $R^1$ have the meanings given above and $R^2$ represents methyl, ethyl, n-propyl, i-propyl, n-butyl, i-butyl, sec.-butyl and tert.-butyl, and $R^3$ represents hydrogen, methyl, ethyl, n-propyl, i-propyl, n-butyl, i-butyl, sec.-butyl and tert.-butyl.

Particularly preferably used compounds of the formula (I) are those in which

X represents oxygen,

R represents methoxy, ethoxy or n-propoxy, $R^1$ represents i-propyl, i-butyl, sec.-butyl, tert.-butyl or n-butyl, $R^2$ represents hydrogen, methyl, ethyl, n-propyl or i-propyl and $R^3$ represents methyl, ethyl, n-propyl or i-propyl, or X, R and $R^1$ have the meanings given above and $R^2$ represents methyl, ethyl, n-propyl or i-propyl and $R^3$ represents hydrogen, methyl, ethyl, n-propyl or i-propyl.

Very particularly preferably used compounds of the formula (I) are those in which X represents oxygen, R represents ethoxy, $R^1$ represents i-propyl, sec.-butyl, tert.-butyl, i- or n-butyl, $R^2$ represents hydrogen, methyl or ethyl and $R^3$ represents methyl, ethyl or i-propyl or X, R and $R^1$ have the meanings given above and $R^2$ represents methyl or ethyl and $R^3$ represents hydrogen, methyl, ethyl or i-propyl.

The active compounds to be used according to the invention of the formula (I) are known and/or can be prepared in a simpler manner by known methods (see, for example, EP-OS (European Published Specification No.) 4,931, DE-AS (German Published Specification No.) 2,040,579, DE-AS (German Published Specification No.) 2,122,636 (=U.S. Pat. No. 3,828,161), DE-AS (German Published Specification No.) 2,627,935. Thus, for example, 2-amino-thiophene derivatives can be reacted with isocyanates or isothiocyanates according to the following equation:

$$\begin{array}{c} R^2 \diagdown \quad \diagup COR \\ \diagup\diagdown \\ R^3 \diagup S \diagdown NH_2 \end{array} + XCN-R^1 \longrightarrow$$

$$\begin{array}{c} R^2 \diagdown \quad \diagup COR \\ \diagup\diagdown \\ R^3 \diagup S \diagdown NH-CX-NHR^1 \end{array}$$

The reaction is usually carried out under atmospheric pressure and at a temperature of 20° C. to 70° C., if appropriate in the presence of an auxiliary base and in the presence of inert diluents, such as, for example, toluene, chloroform and pyridine.

The active compounds to be used according to the invention have a powerful selective fungicidal action and can be employed in practice for combating undesired Botrytis fungi. The active compounds are suitable for use as Botrytis agents in plant protection.

The active compounds to be used according to the invention display particularly good activity, for example, against *Botrytis cinerea,* the causative organism of grey mould in beans, lettuce, strawberries and grapevines, and they are preferably employed in grapevines, strawberries and lettuce.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides, and herbicides, and as mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on, etc.

In the treatment of parts of plants, the active compound concentrations in the use forms can be varied within a relatively wide range. They are in general between 1 and 0.0001% by weight, preferably between 0.5 and 0.001%.

EXAMPLE A

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, a clearly superior activity compared with the prior art (A) is shown by, for example, the compounds according to preparation Examples (1), (4), (14), (16) and (18).

TABLE A

Botrytis test (bean)/protective

| Active compound | | Infestation in % at an active compound concentration of 100 ppm |
|---|---|---|
| CH₃―C(=)―COO―C₂H₅ / CH₃―C(=)―NH―CO―NH―CH₃ with S bridge (known) | (A) | 29 |

TABLE A-continued

Botrytis test (bean)/protective

| Active compound | | Infestation in % at an active compound concentration of 100 ppm |
|---|---|---|
| CH₃-C(=C(COO-C₂H₅)-NH-CO-NH-CH(CH₃)₂)-S-C(CH₃)= [thiophene with CH₃, CH₃, COO-C₂H₅, NH-CO-NH-CH(CH₃)₂] | (1) | 2 |
| [thiophene with C₂H₅, CH₃, COO-C₂H₅, NH-CO-NH-CH(CH₃)₂] | (4) | 2 |
| [thiophene with CH₃, C₂H₅, COO-C₂H₅, NH-CO-NH-C(CH₃)₃] | (14) | 6 |
| [thiophene with CH₃, H, COO-C₂H₅, NH-CO-NH-CH(CH₃)₂] | (16) | 8 |
| [thiophene with CH₃, H, COO-C₂H₅, NH-CO-NH-CH(CH₃)(CH₂CH₃)] | (18) | 7 |

EXAMPLE B

Botrytis test (grapevine)/protective
Solvent: 4.7 parts by weight of acetone
Dispersant: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, a clearly superior activity compared with the prior art is shown by, for example, the compounds according to preparation Examples 1, 4, 14, 3, 8 and 9.

TABLE B

Botrytis test (grapevine)/protective

| Active compound | Infestation is % at an active compound concentration of 25 ppm |
|---|---|
| (known) H₃C, H₃C-thiophene-S-... C(=O)-O-C₂H₅, NH-C(=O)-NH-CH₃ | 32 |
| (according to the invention) | |

TABLE B-continued

Botrytis test (grapevine)/protective

| Active compound | | Infestation is % at an active compound concentration of 25 ppm |
|---|---|---|
| (structure: 4,5-dimethyl-3-ethoxycarbonyl-2-thienyl, NH-CO-NH-CH(CH₃)₂) | (1) | 14 |
| (structure: 5-methyl-4-ethyl-... ethoxycarbonyl-thienyl, NH-CO-NH-C(CH₃)₂H) | (4) | 5 |
| (structure: 4-methyl-5-ethyl-3-ethoxycarbonyl-thienyl, NH-CO-NH-C(CH₃)₃) | (14) | 24 |
| (structure: 5-isopropyl-3-ethoxycarbonyl-thienyl, NH-CO-NH-CH(CH₃)₂) | (3) | 10 |
| (structure: 5-ethyl-3-ethoxycarbonyl-thienyl, NH-CO-NH-CH(CH₃)₂) | (8) | 10 |
| (structure: 5-ethyl-3-ethoxycarbonyl-thienyl, NH-CO-NH-CH(CH₃)-CH₂-CH₃) | (9) | 7 |

PREPARATION EXAMPLES

Example 1

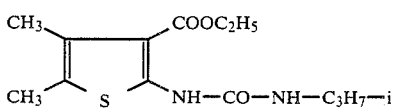

5 g (0.05 mol) of isopropyl isocyanate are added to 7 g (0.035 mol) of 2-amino-3-ethoxycarbonyl-4,5-dimethylthiophene (see Chem. Ber. 99, 94–100 (1966)) in 150 ml of dry pyridine, and the mixture is heated to 70° C. for 12 hours. After cooling, the mixture is stirred into 1 l of dilute hydrochloric acid, and the precipitate is filtered off under suction and recrystallized from ethanol/water.

5.9 g (59.6% of theory) of 1-(4,5-dimethyl-3-ethoxycarbonyl-2-thienyl)-3-isopropyl-urea of melting point 135° C. are obtained.

The following compounds of the formula (I) can be prepared analogously to Example 1:

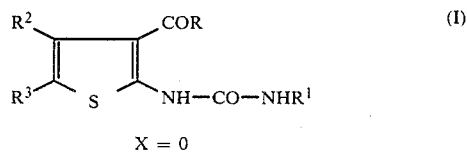

X = O

TABLE 1

| Example No. | R | R¹ | R² | R³ | Melting point [°C.] |
|---|---|---|---|---|---|
| 2 | —OC$_2$H$_5$ | —C$_4$H$_9$—n | —CH$_3$ | —CH$_3$ | 78 |
| 3 | —OC$_2$H$_5$ | —C$_3$H$_7$—i | H | —C$_3$H$_7$—i | 91 |
| 4 | —OC$_2$H$_5$ | —C$_3$H$_7$—i | —C$_2$H$_5$ | —CH$_3$ | 139–140 |
| 5 | —OC$_2$H$_5$ | —C$_4$H$_9$—n | —C$_2$H$_5$ | —CH$_3$ | 72 |
| 6 | —OC$_2$H$_5$ | —C$_4$H$_9$—t | H | —C$_3$H$_7$—i | 113–114 |
| 7 | —OC$_2$H$_5$ | —C$_4$H$_9$—s | H | —C$_3$H$_7$—i | 122 |
| 8 | —OC$_2$H$_5$ | —C$_3$H$_7$—i | H | —C$_2$H$_5$ | 104 |
| 9 | —OC$_2$H$_5$ | —C$_4$H$_9$—s | H | —C$_2$H$_5$ | 109 |
| 10 | —OC$_2$H$_5$ | —C$_4$H$_9$—t | H | —C$_2$H$_5$ | 146 |
| 11 | —OC$_2$H$_5$ | —C$_4$H$_9$—t | —C$_2$H$_5$ | —CH$_3$ | 169 |
| 12 | —OC$_2$H$_5$ | —C$_4$H$_9$—s | —C$_2$H$_5$ | —CH$_3$ | 139 |
| 13 | —OC$_2$H$_5$ | —C$_3$H$_7$—i | —CH$_3$ | —C$_2$H$_5$ | 82 |
| 14 | —OC$_2$H$_5$ | —C$_4$H$_9$—t | —CH$_3$ | —C$_2$H$_5$ | 152 |
| 15 | —OC$_2$H$_5$ | —C$_4$H$_9$—s | —CH$_3$ | —C$_2$H$_5$ | 01 |
| 16 | —OC$_2$H$_5$ | —C$_3$H$_7$—i | H | —CH$_3$ | 112 |
| 17 | —OC$_2$H$_5$ | —C$_4$H$_9$—t | H | —CH$_3$ | 140 |
| 18 | —OC$_2$H$_5$ | —C$_4$H$_9$—s | H | —CH$_3$ | 118 |
| 19 | —OC$_2$H$_5$ | —C$_3$H$_7$—i | —CH$_3$ | H | 121 |
| 20 | —OC$_2$H$_5$ | —C$_4$H$_9$—i | —CH$_3$ | H | 92 |
| 21 | —OC$_2$H$_5$ | —C$_4$H$_9$—s | —CH$_3$ | H | 87 |
| 22 | —OC$_2$H$_5$ | —C$_4$H$_9$—t | —CH$_3$ | H | 137 |

It will be understood that the specification and examples are illustrative but not limitative of the present invention and that other embodiments within the spirit and scope of the invention will suggest themselves to those skilled in the art.

We claim:

1. A method of combating Botrytis fungi which comprises applying to such fungi a fungicidally effective amount of a thienylurea derivative of the formula

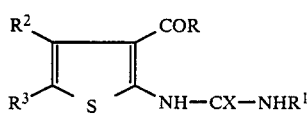

in which
X is oxygen,
R is C$_1$–C$_4$-alkoxy,
R$^1$ is C$_3$–C$_4$-alkyl, and
R$^2$ and R$^3$ each independently is C$_1$–C$_4$-alkyl and one of them may also be hydrogen.

2. The method according to claim 1, in which
R is methoxy, ethoxy, n-propoxy, i-propoxy, n-butoxy, i-butoxy, s.-butoxy or t.-butoxy,
R$^1$ represents n-propyl, i-propyl, n-butyl, i-butyl, sec.-butyl or tert.-butyl,
R$^2$ is hydrogen, methyl, ethyl, n-propyl, i-propyl, n-butyl, i-butyl, s.-butyl or t.-butyl, and
R$^3$ is methyl, ethyl, n-propyl, i-propyl, n-butyl, i-butyl, s.-butyl or t.-butyl.

3. The method according to claim 1, in which
R is methoxy, ethoxy, n-propoxy, i-propoxy, n-butoxy, i-butoxy, s.-butoxy or t.-butoxy,
R$^1$ is n-propyl, i-propyl, n-butyl, i-butyl, s.-butyl or t.-butyl,
R$^2$ is methyl, ethyl, n-propyl, i-propyl, n-butyl, i-butyl, s.-butyl or t.-butyl, and
R$^3$ is hydrogen, methyl, ethyl, n-propyl, i-propyl, n-butyl, i-butyl, s.-butyl or t.-butyl.

4. The method according to claim 1, in which
R is methox, ethoxy or n-propoxy,
R$^1$ is i-propyl, i-butyl, s.-butyl, t.-butyl or n-butyl,
R$^2$ is hydrogen, methyl, ethyl, n-propyl or i-propyl, and
R$^3$ is methyl, ethyl, n-propyl or i-propyl.

5. The method according to claim 1, in which
R is methoxy, ethoxy or n-propoxy,
R$^1$ is i-propyl, i-butyl, s.-butyl, t.-butyl, or n-butyl,
R$^2$ is methyl, ethyl, n-propyl or i-propyl, and
R$^3$ is hydrogen, methyl, ethyl, n-propyl or i-propyl.

6. The method according to claim 1, in which
R is ethoxy,
R$^1$ is i-propyl, s.-butyl, t.-butyl, i- or n-butyl,
R$^2$ is hydrogen, methyl or ethyl, and
R$^3$ is methyl, ethyl or i-propyl.

7. The method according to claim 1, in which
R is ethoxy,
R$^1$ is i-propyl, s.-butyl, t.-butyl, i or n-butyl,
R$^2$ is methyl or ethyl, and
R$^3$ represents hydrogen, methyl, ethyl or i-propyl.

8. The method according to claim 1, wherein the urea derivative is 1-(4,5-dimethyl-3-ethoxycarbonyl-2-thienyl)-3-isopropyl urea of the formula

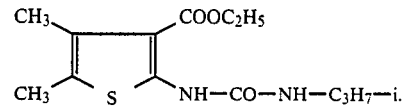

9. The method according to claim 1, wherein the urea derivative is 1-(5-isopropyl-3-ethoxycarbonyl-2-thienyl)-3-isopropyl urea of the formula

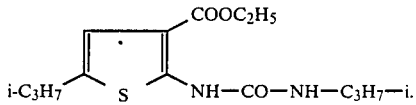

10. The method according to claim 1, wherein the urea derivative is 1-(4-ethyl-5-methyl-3-ethoxycarbonyl-2-thienyl)-3-isopropyl urea of the formula

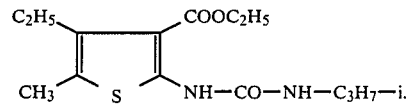

11. The method according to claim 1, wherein the urea derivative is 1-(5-ethyl-3-ethoxycarbonyl-2-thienyl)-3-isopropyl urea of the formula

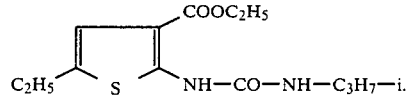

12. The method according to claim 1, wherein the urea derivative is 1-(5-ethyl-3-ethoxycarbonyl-2-thienyl)-3-s.-butyl urea of the formula

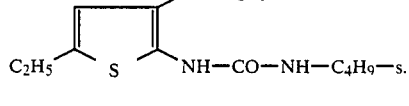

13. The method according to claim 1, wherein the thienylurea derivative is applied to said fungi on grapevines or to a field in which grapevines are growing.

* * * * *